US009180265B2

(12) United States Patent
Gutiérrez Fonseca et al.

(10) Patent No.: US 9,180,265 B2
(45) Date of Patent: Nov. 10, 2015

(54) COMPACT DEVICE FOR CONTROLLING AND MODIFYING THE PRESSURE OF A GAS OR A MIXTURE OF GASES

(75) Inventors: Jaime Eduardo Gutiérrez Fonseca, Barranquilla (CO); Oscar Omar Ovalle Orejarena, Barranquilla (CO); Antonio Bula Silvera, Barranquilla (CO)

(73) Assignees: Fundacion Universidad Del Norte, Puerto Rico (CO); Socieded Biotecnologia y Bioingenieria Core S.A., Barranquilla (CO)

( * ) Notice: Subject to any disclaimer, the term of this patent is extended or adjusted under 35 U.S.C. 154(b) by 662 days.

(21) Appl. No.: 13/381,445

(22) PCT Filed: Jul. 2, 2010

(86) PCT No.: PCT/IB2010/001642
§ 371 (c)(1),
(2), (4) Date: Mar. 19, 2012

(87) PCT Pub. No.: WO2011/001277
PCT Pub. Date: Jan. 6, 2011

(65) Prior Publication Data
US 2012/0160242 A1  Jun. 28, 2012

(30) Foreign Application Priority Data
Jul. 2, 2009  (CO) .................................. 09-068500

(51) Int. Cl.
*A61M 11/00*  (2006.01)
*A61M 16/00*  (2006.01)
*A61M 16/06*  (2006.01)

(52) U.S. Cl.
CPC ........... *A61M 16/00* (2013.01); *A61M 16/0666* (2013.01); *A61M 2205/3331* (2013.01); *A61M 2205/3348* (2013.01)

(58) Field of Classification Search
CPC .. A61M 16/16; A61M 16/162; A61M 11/041
USPC ............. 128/207.18, 200.26, 207.13, 204.12, 128/204.18, 206.27; 141/95, 198; 137/414, 137/386, 393, 893, 895
See application file for complete search history.

(56) References Cited

U.S. PATENT DOCUMENTS 3,741,230 A * 6/1973 Samuels ....................... 137/805
3,827,433 A   8/1974 Shannon
(Continued)

FOREIGN PATENT DOCUMENTS

CN  2877741   3/2007
DE  29 29 996  2/1981
(Continued)

OTHER PUBLICATIONS

"2005 American Heart Association (AHA) Guidelines for Cardiopulmonary Resuscitation (CPR) and Emergency Cardiovascular Care (ECC) of Pediatric and Neonatal Patients: Neonatal Resuscitation Guidelines," American Heart Association, American Academy of Pediatrics, article, Pediatrics, vol. 117, No. 5, pp. 1029-1038 (May 2006).
(Continued)

*Primary Examiner* — Steven Douglas
(74) *Attorney, Agent, or Firm* — Lempia Summerfield Katz LLC

(57) ABSTRACT

A device for controlling the pressure of a gas in a circuit via the generation of bubbles through a liquid, which is used to produce a continuous positive airway pressure (CPAP), is provided. The device includes a container containing a liquid and a bubble tube with one end located outside the liquid connected to a device connected to a patient's respiratory tract and the other end located within the liquid. The device also includes at least one hose for adjusting the level of liquid in the container.

12 Claims, 10 Drawing Sheets

(56) References Cited

U.S. PATENT DOCUMENTS

| | | | | |
|---|---|---|---|---|
| 4,073,310 | A | * | 2/1978 | Mikule et al. ............... 137/389 |
| 5,193,646 | A | * | 3/1993 | Horikawa et al. ............ 184/7.4 |
| 5,271,391 | A | | 12/1993 | Graves et al. |
| 5,319,954 | A | * | 6/1994 | Koeda et al. ................. 73/19.1 |
| 6,588,458 | B2 | * | 7/2003 | Rodgers ........................ 141/9 |
| 6,684,902 | B1 | * | 2/2004 | Zinn et al. .................... 137/393 |
| 2005/0072470 | A1 | | 4/2005 | Jacobs et al. |

FOREIGN PATENT DOCUMENTS

| | | |
|---|---|---|
| ES | 2 262 476 | 12/2006 |
| ES | 2 319 832 | 5/2009 |
| WO | WO 81/00212 | 2/1981 |

OTHER PUBLICATIONS

Beatrice M. Stefanescu, M.D. et al., "A Randomized, Controlled Trial Comparing Two Different Continuous Positive Airway Pressure Systems for the Successful Extubation of Extremely Low Birth Weight Infants," article, Pediatrics, vol. 112, No. 5, pp. 1031-1038 (Nov. 2003).

Colin J. Morley et al., "Advances in Neonatal Resuscitation: Supporting Transition," article, Arch. Dis. Child Fetal Neonatal Ed., vol. 93, No. 5, pp. F334-F336 (Sep. 2008).

International Search Report dated Oct. 18, 2010, issued in corresponding international application No. PCT/IB10/001642.

Written Opinion dated Oct. 18, 2010, issued in corresponding international application No. PCT/IB10/001642.

Translation of International Preliminary Report on Patentability dated Dec. 24, 2010, issued in corresponding international application No. PCT/IB10/001642.

* cited by examiner

FIG. 10
Fig. 10a
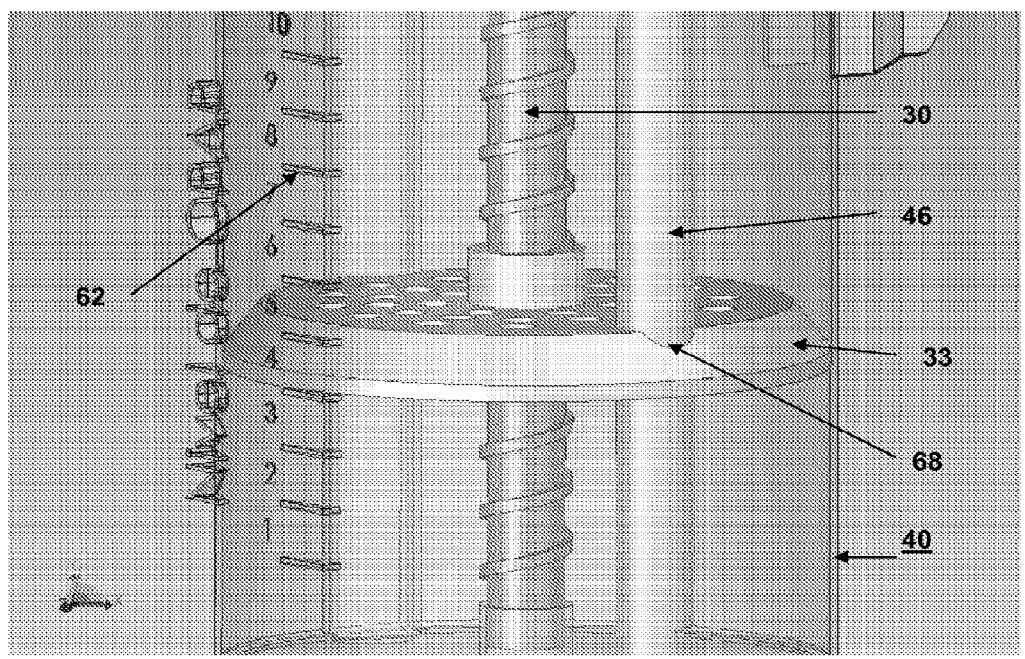
Fig. 10b
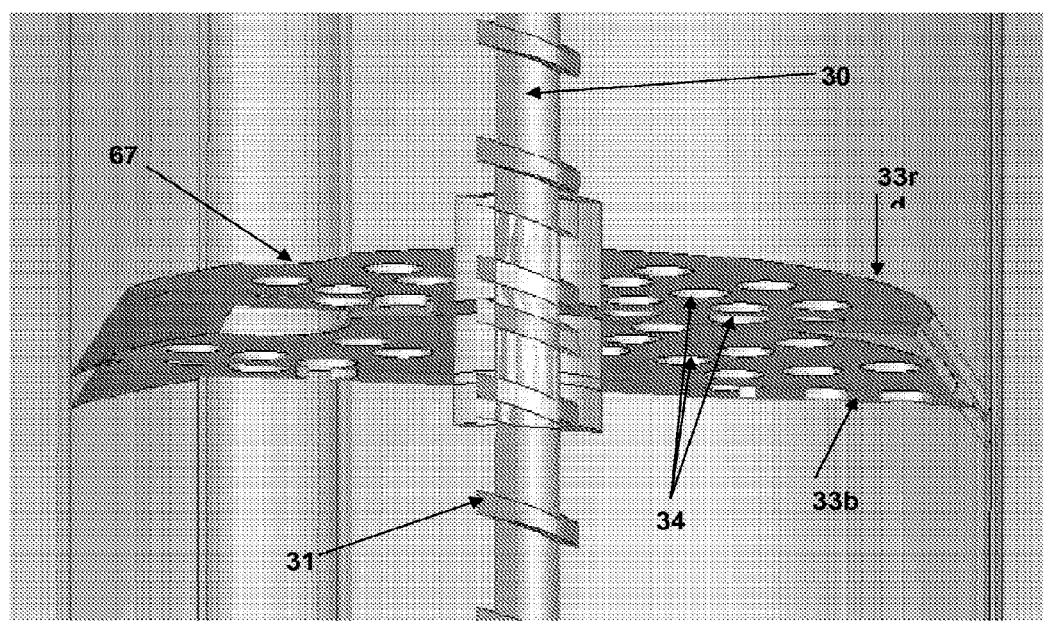

COMPACT DEVICE FOR CONTROLLING AND MODIFYING THE PRESSURE OF A GAS OR A MIXTURE OF GASES

1. RELATED APPLICATION DATA

This U.S. national phase application is based on International Application No. PCT/IB2010/001642 filed on Jul. 2, 2010, which claimed priority to Colombian Patent Application No. 09-068500 filed on Jul. 2, 2009. Priority benefit of these earlier filed applications is hereby claimed, and the full disclosures of these earlier filed applications are hereby incorporated by reference herein.

2. FIELD OF THE INVENTION

This invention relates to controlling gas pressure in a circuit by generating bubbling through a liquid, this effect being used to produce a continuous positive airway pressure.

3. DESCRIPTION OF THE ART

The present invention relates to gas pressure control through devices that are designed to maintain a stable pressure in patients with respiratory failure, specifically in newborns or infants. Therefore, it must be considered that continuous distending pressure is defined as a positive gas pressure across the airway or sufficient enough to keep the alveoli open or distended and held during the natural breathing cycle. The natural cycle consists of inspiration, exchange and expiration. When this phenomenon occurs while the patient breathes spontaneously, it is called CPAP (Continuous Positive Airway Pressure) and when it occurs during the use of mechanical ventilation (connected to a mechanical ventilator) it is called PEEP (Positive end-expiratory Pressure), since positive pressure is applied at the end of expiration. This method is used to increase pressure in the lungs above atmospheric pressure.

PEEP and CPAP are used to correct respiratory distress such as atelectasis (collapse and related lung dysfunction), or when there is decreased functional residual capacity (percentage of lung capacity with the lungs above the minimum necessary to survive), or alteration of ventilation perfusion (alteration in the amount of gas reaching the alveoli and blood supply reaching the lungs) or pulmonary edema (liquid accumulation in lung tissue that hinders gas exchange).

The application of continuous positive airway pressure for the management of hypoxemia (low blood oxygen level) is one of the great breakthroughs in neonatal respiratory therapy. This therapeutic application improves oxygenation by increasing functional residual capacity, thus increasing lung tissue area capable of gas exchange through alveoli recruitment (opening air sacs that are closed). This reduces the imbalance between pulmonary perfusion and gas exchange (intra pulmonary shunt). It also reduces the need to force the lungs to full capacity (functional capacity plus residual capacity), which is beneficial for the patient, since forcing the lungs produces an increase in air entering the lungs.

The technique by which continuous positive pressure is delivered to the nasal airway (NCPAP) is widely known and used in preterm and low birth weight newborns as a preventive measure of respiratory distress syndrome and the need for intubation and mechanical ventilation[1].

[1] "2005 American Heart Association (AHA) Guidelines for Cardiopulmonary Resuscitation (CPR) and Emergency Cardiovascular Care (ECC) of Pediatric and Neonatal Patients: Neonatal Resuscitation Guidelines." Pediatrics, Official Journal of the American Academy of Pediatrics. ISSN 0031-4005, Aug. 28, 2006.

The general mechanism requires placing a mask over nose and mouth, or some "prongs" that are inserted directly into the nostrils of the baby. Either of these two elements are connected to a standard ventilator circuit. The ventilation circuit must maintain a flow of gas pressure above atmospheric pressure by applying resistance to the gas outlet end of the circuit (for example, a water level). This increased pressure forces the gas out of the prongs or mask into the infant's airway. The degree of ventilatory support given is proportional to the level of pressure within the ventilation circuit, measured in centimeters of water. There are no known systems that measure ventilatory support in terms of gas volume passing through the circuit, or the gas pressure in the mask, prongs or lungs.

There are two known traditional ways of applying NCPAP. The first is connecting the ventilatory circuit to a mechanical ventilator machine, which is programmed in order for it not to cycle, but instead to provide continuous positive pressure; the dose being programmed into the machine and measured by a manometer. This mechanism is effective, but its use causes the wear and tear of a piece of mechanical ventilation equipment, and would therefore block its use for other patients who may require it with higher priority. The other method is the "bubble CPAP", of which the schematic diagram shown in FIG. 1 is a typical example. The diagram depicts an oxygen source 1 (not shown) from which gas is supplied through a conventional connection 2 to a mixing chamber 3. Air is supplied to the camera through another inlet 4. The oxygen and air are mixed inside the chamber and they flow through a conventional humidifier 5, in which the gas mixture is humidified to the required moisture level. The initial segment of a conventional ventilation tube 6a is connected to the outlet of the humidifier. The final segment of this first tube is connected to a device which creates a pressure differential to the patient with a conventional face mask 7 or with conventional nasal prongs 8. The face mask 7 or the nasal prongs 8 is (are) then connected to the initial segment of another conventional ventilation tube 6b, whose other free end is immersed in a liquid 9, or connected to the initial end of some kind of rigid tube 10 whose other end is immersed in a liquid, which may be water, saline, dextrose in distilled water or other liquid within a container 12. This container can have a lid 17, with holes for the inlet of tube 18, or the air outlet 19. This causes the gas mixture to flow from the humidifier 5, through the vent tube 6a, to the facemask 7 or nasal prongs 8, and then onto the lungs of the newborn. The air not inhaled is passed through the second vent tube 6b and out the open and submerged end of vent tube 6b, or the free and submerged end of rigid tube 10 where the gas mixture forms bubbles 11 that escape to the surface of liquid 9 and finally dissolve into the environment. In this system, the depth to which the free end of the rigid tube 10 is submerged, with respect to the surface of the liquid in the container, shall determine the pressure level in the ventilator circuit 6, and therefore in the nasal prongs 8 or face mask 7, which accordingly determines the level of ventilatory support supplied to the newborn. This level is measured in centimeters, usually on a scale 13 printed, drawn or attached to the wall of the container, or on the rigid tube itself that is half submerged in the liquid, so that the position of the submerged end of the vent tube, can be read in reference to this scale.

Typically, the pressure in the ventilation circuit 6 can vary anywhere between 1 to 10 centimeters of water, by adjusting the depth of the bubble point to the surface of the liquid 9. In other words, the liquid level is static and what varies is the tube. Normally, after placing the distal end of the ventilatory circuit at the desired depth, it is then fixed by any auxiliary means such as gaging tubes 14, slots 15, extensions or wedges 16. Additionally, you can connect a gauge 66 to measure pressure within the ventilatory circuit 6. However, the means by which the depth of immersion of the distal end of the ventilatory circuit in the liquid is changed, is unstable. Even in those versions having locks, extensions, or wedges, the resistance thereof does not guarantee that the same level of immersion prevails, and therefore, undesirable changes may arise in the level of ventilatory support delivered to the patient.

Additionally, existing systems are not suitable for use in transportation, as the liquid level changes greatly with the movement of a vehicle, and may even spill liquid from the container, resulting in pressure loss and disruption of the therapy. This is very relevant since the main users of bubble CPAP therapy are low birthweight newborns, of which a large proportion are born far away from the high-level care facilities, requiring ambulance transportation, time during which CPAP therapy can be life-saving. A CPAP device is thus required which may be safely used during vehicle transportation.

4. BRIEF DESCRIPTION OF THE DRAWINGS

The invention will be described by the following drawings wherein reference numbers are included to identify the constituent parts:

FIG. 10 is an extension of the liquid level stabilization mechanism in a preferred embodiment of the present invention.

5. BRIEF DESCRIPTION OF THE INVENTION

The present invention consists of a device for controlling and modifying the pressure of a gas or a mixture thereof, within a system in which the pressure and changes thereof are generated by gas bubbling through a liquid but, unlike prior art, the pressure varies changing the liquid level.

In a preferred embodiment, the device comprises a liquid inlet hose having a shutoff valve, a container, a lid, a fixed bubble tube and an overflow tube. The inlet hose allows adjusting the liquid level in the container, which thus varies the amount of liquid over the bubble point, and hence the pressure generated. In another preferred embodiment, the device also has an element of liquid level stabilization comprising a screw and double perforated platform, which can move over the length of the screw, a liquid outlet hose with a shutoff valve and a heating and humidifying internal container. This system prevents the liquid level from varying due to sudden device movements such as inside a moving vehicle.

Unlike prior art, the present invention provides a modification of ventilatory support by means of varying the liquid level in the container and not by varying the bubble tube height. This provides improved safety for controlling respiratory therapy in patients. Additionally, the present invention provides the possibility that the device may be used in moving vehicles using level stabilizers that prevent the variation of the respiratory system pressure due to movement of the device.

6. DETAILED DESCRIPTION OF THE INVENTION

Figure 1:
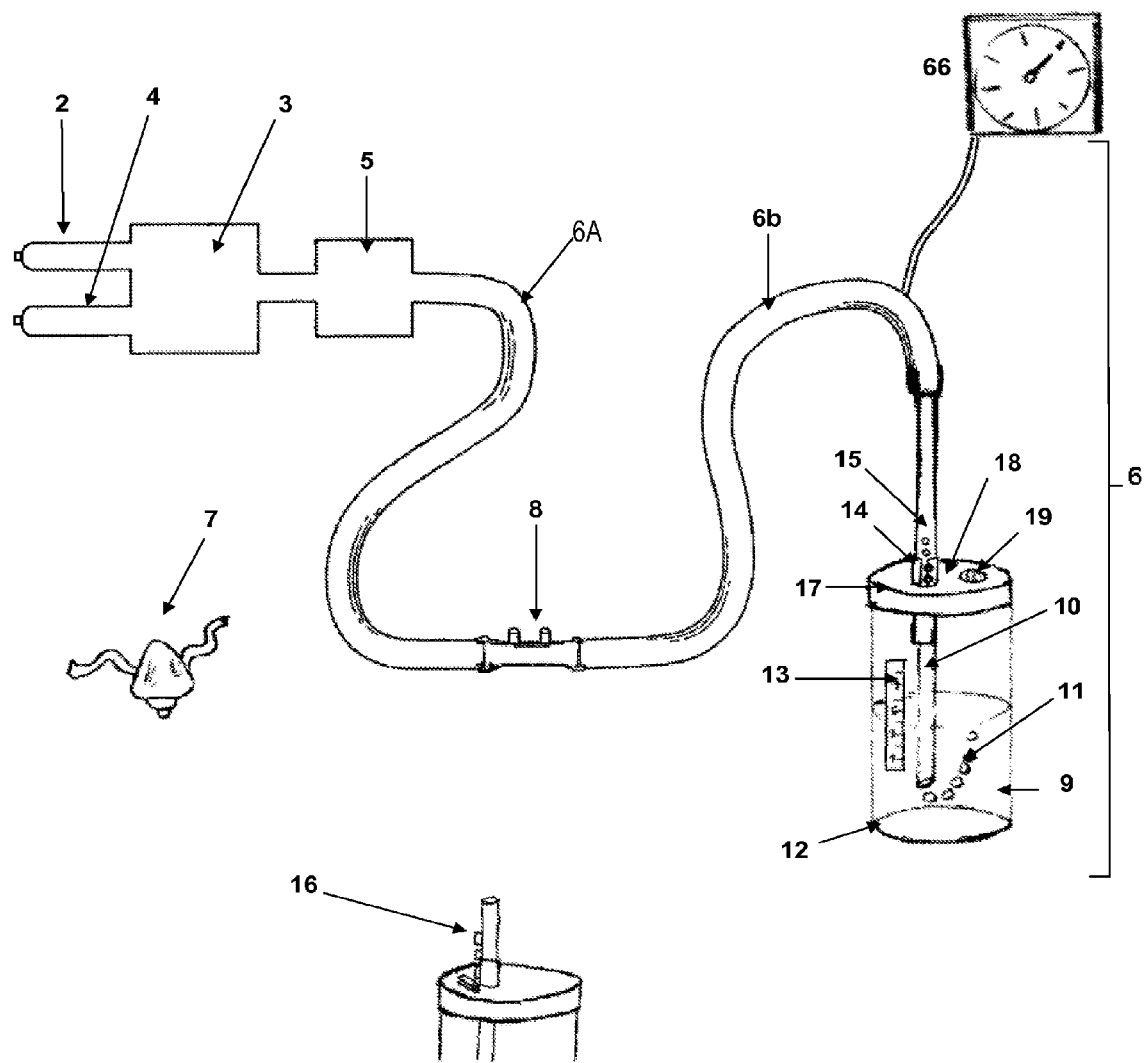
FIG. 1 is a schematic diagram of a conventional circuit for bubble CPAP devices known in the art.
Figure 2:
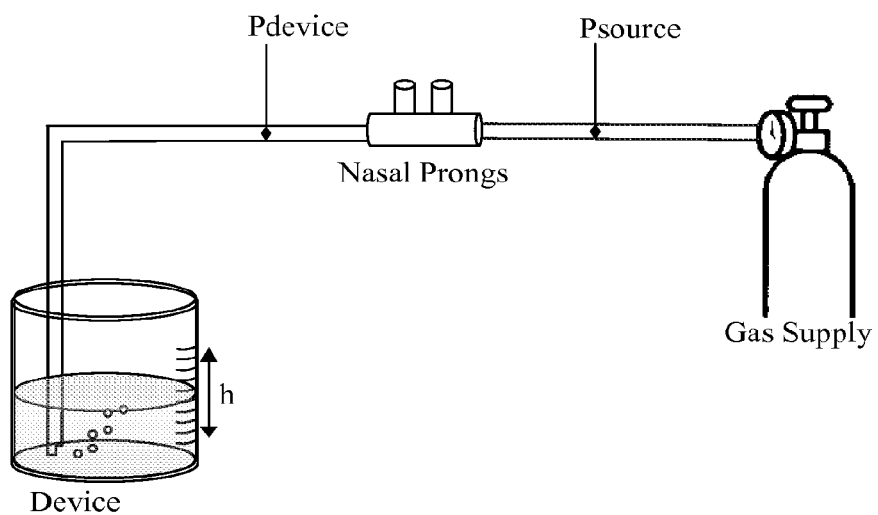
FIG. 2 is a schematic figure of one embodiment of the invention where the claimed device is connected to nasal prongs and to the gas source.

Referring to FIG. 2, a scheme is shown of the airflow generated when connecting an embodiment of the present invention to a respiratory tool for a patient connected to a gas source (in FIG. 2, this tool are nasal prongs, but it may also be face masks, endotracheal tubes or other delivery devices). A gas source may include a single gas or mixture of two or more hospital gases used in patient care or treatment who require breathing assistance. The outlet pressure of gas flows at a given pressure ($P_{source}$) towards the nasal prongs. In a patient's expiration phase, the pressure which the liquid exerts on the gas ($P_{device}$), which is the same as the one exerted on the patient's lungs, is slightly higher than atmospheric pressure (this value depends on the liquid volume amount inside the device container of the present invention (the liquid level is represented as h–)). Thus, the pressure exerted by the device on the lungs ($P_{device}$) does not allow the patient's lungs to collapse.

Figure 3:
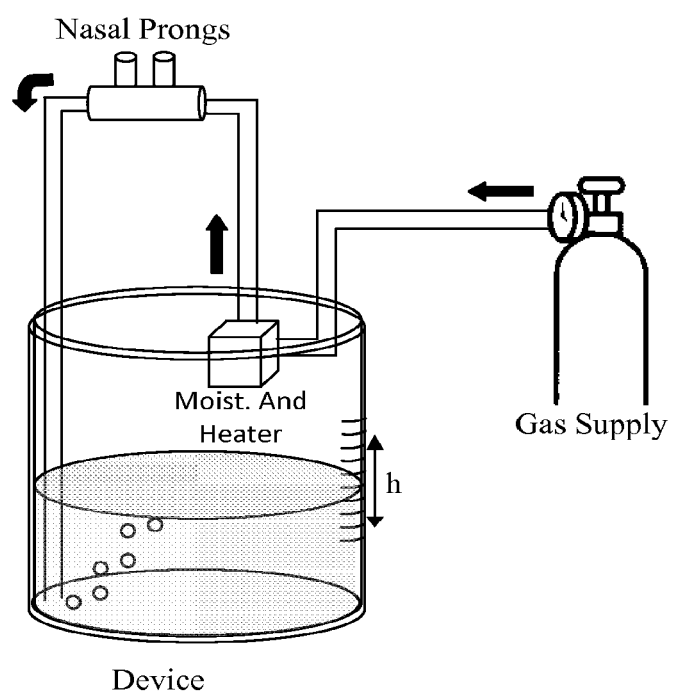
FIG. 3 is a schematic figure of another embodiment of the invention where the device of the present invention has a humidifier, heater and a nasal prongs connected to the gas source.

In a most preferred embodiment of the present invention, illustrated in FIG. 3, a humidifying and heating device incorporated in the container is additionally observed. This Figure shows the flow of air generated when the humidifier and heater device is present. In this embodiment, the air flow is similar to that shown in FIG. 2, but with the difference that the air flow passing through the nasal prongs is pre-heated and humidified to a predetermined level (established in various treatment protocols). Here, the pressure generated in the prongs is equally controlled by the level of liquid in the device container of the present invention.

Figure 4:
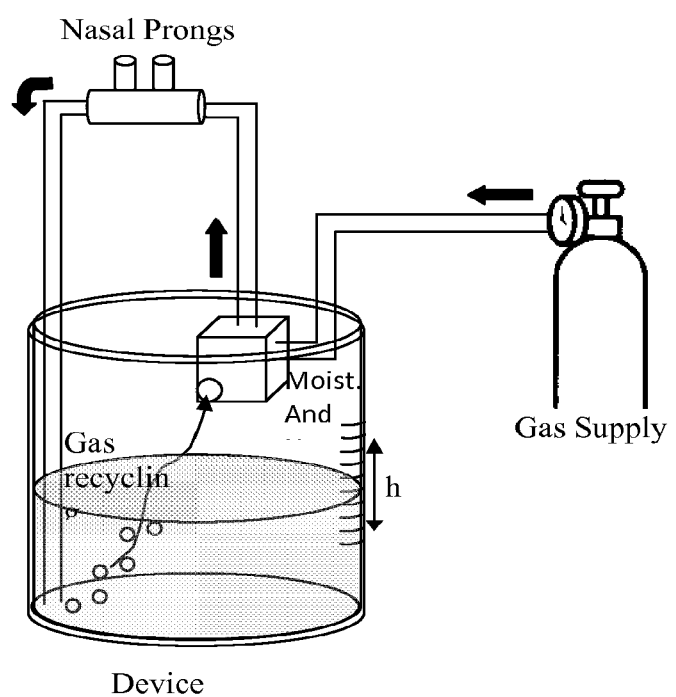
FIG. 4 is a schematic figure of another embodiment of the invention where the device of the present invention recycles the gas within the system.

FIG. 4 shows the scheme for another preferred embodiment, similar to that shown in FIG. 3, but with the feature that the gas bubbling through the liquid in the container, returns to the vent circuit through an orifice or venturi on the humidifier and heater device. The operation details of these schemes are described in detail in the description of the figures below.

Figure 5:
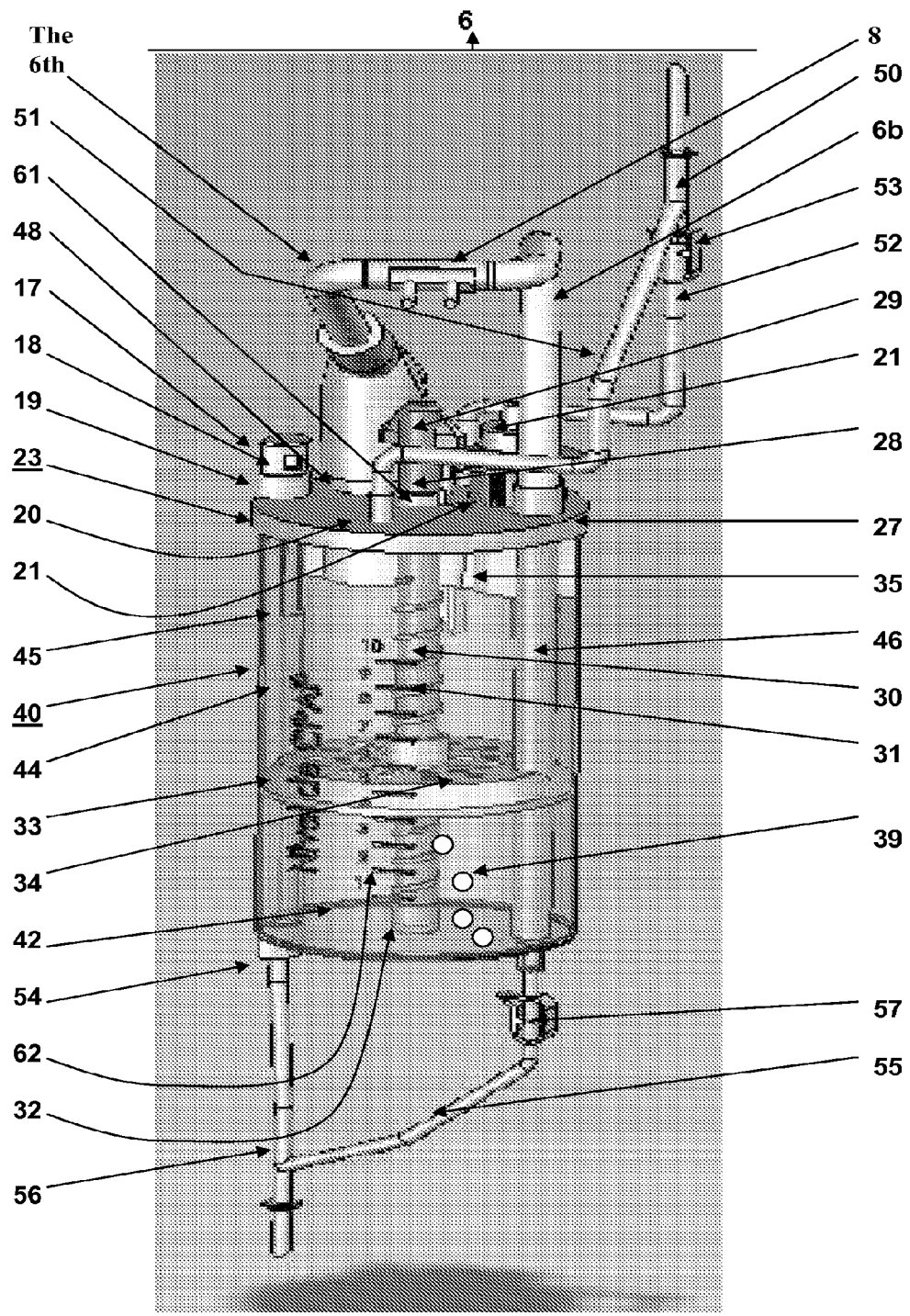
FIG. 5 is a schematic diagram of the isometric frontal view of a preferred embodiment of the invention.

FIG. 5 shows the preferred embodiment of the present invention schematically in FIG. 3, in which the device is formed by a liquid inlet hose 50 with a bypass valve 53, a container 40, a lid 23, a bubble tube 56, an overflow and pressure stabilization tube 44, a liquid level stabilization device comprising a rotating shaft 30 and a perforated platform 33, a liquid outlet hose 55 having a shut-off valve 57, an inner humidifying and heating container 35, conventional connection pipes connected to the holes in the lid of the device and to the nasal prongs 8.

The device of the present invention is connected to a liquid source (not shown) via a hose 50. This hose is divided into two branches, the fill hose 52 of the inner humidifier and heater container 35 and the level increase hose 51, which has a closure valve 53. The far end of the filling hose 52 is connected to the hole 20 of lid 23, which connects with the inner container 35. The far end of the level increase hose 51 is connected to hole 26 of lid 23.

The upper end of the overflow and pressure stabilization tube 44 is connected to the pressurization hole 19 located on the bottom face of lid 23. The bottom end of the overflow tube 44 is connected to the overflow hole 60 located at the bottom of container 40. The overflow tube 44 has the overflow hole 45 located towards the bottom of container 40, which allows, in any case, for the liquid level to overflow. In a preferred embodiment, this height is 10 centimeters.

The device shown in FIG. 5 is connected to a ventilator circuit wherein the gas source is connected through a conventional vent hose to the connector for hospital gas sources 21 located on lid 23. Hole 48 is connected to the end of vent hose 6A which is further connected to the nasal prongs 8. The other end of the prongs 8 is connected to a vent hose 6b which connects to hole 25 of lid 23. At the end of bubble tube 46, a bubble hole 47 is found, through which bubbles come out 39. Given bubble tube 46 is fixed, the level of CPAP provided is set by changing the liquid level 42 within container 40. Thus, the higher the liquid level, the deeper the bubble hole 47 is submerged, thus generating higher levels of CPAP.

Container 40 shown in FIG. 5 is made of conventional materials such as glass or plastic, manufactured by injection or machining.

Figure 6:
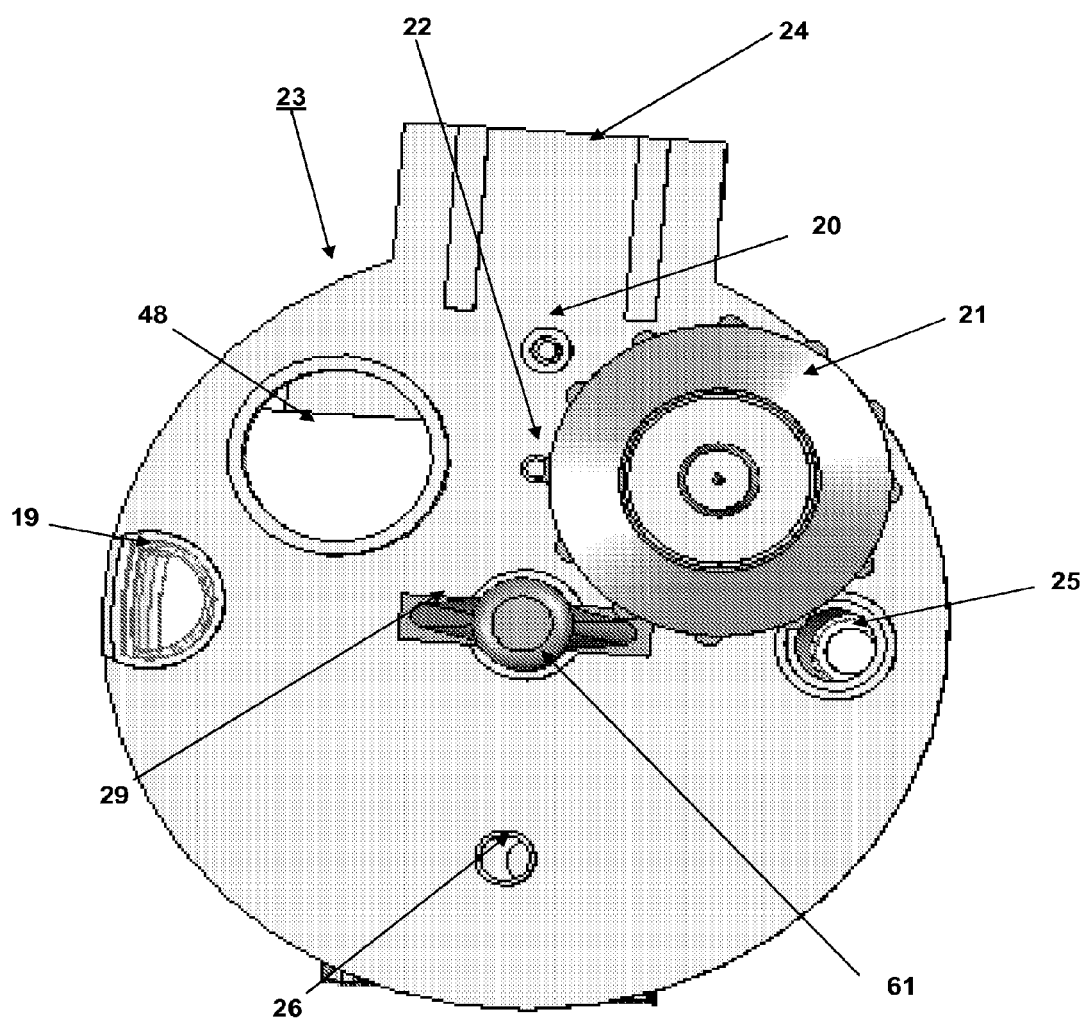
FIG. 6 is a top surface view of the apparatus lid shown in FIG. 5.

FIG. 6 shows a view of the upper face of lid 23, which screws on to the top opening of container 40. A pressurization hole 19 is found on the top of lid 23, which ensures that when the container 40 is closed with lid 23, the pressure on the surface of the liquid inside the container 40 is equal to atmospheric pressure. A security cap 17 can be found over said pressurization hole 19 (see FIG. 9), said cap having lateral openings 18 (see FIG. 9), whose function is to prevent the entry of small solids within the container 40. Lid 23 also has a hole 26 for connecting the liquid level increase hose 50 through which the container 40 is filled. The lid also has an anchor hole 61 for the anchored rotating shaft 30 which is part of the level stabilizer 33. In the embodiment shown in FIG. 6, hole 61 is located in the center of lid 23. The lid additionally has a hole 25 to which the end of the conventional vent tube is connected to and which further connects to one end of the prongs 8 or gas mask 7. The edge of the lid has a conventional support for a hospital stand 24, which serves to secure the device to a hospital or ambulance stand. The lid has a hole 20 for the entry of liquid into the internal humidification and heating container 35. The lid also has a hole 22 for inserting an electrical resistance 36 inside the inner container 35. Lid 23 has a conventional connector for hospital gas sources 21, which has a gas mixing venturi, which as already explained, mixes gases in the air with the gas entering from the gas source. The lid further has a hole 48 for connecting the front end of the vent tube which is further connected to one end of the prongs 8 or gas mask 7 with the inner container 35.

Figure 7:
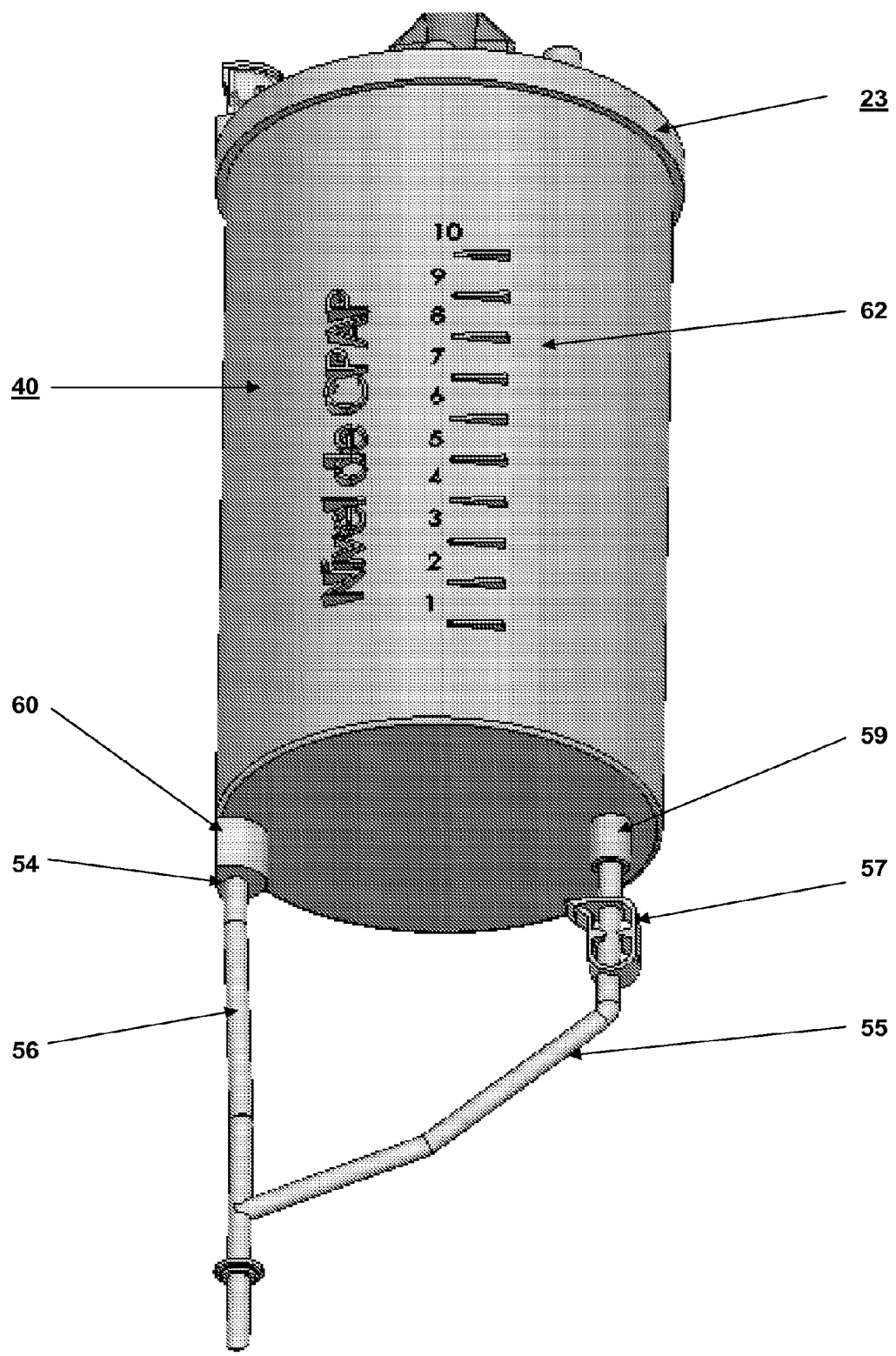
FIG. 7 is an isometric view of the bottom of the apparatus shown in FIG. 5.

FIG. 7 shows the bottom of container 40 having an outlet 60 to which overflow tube 44 is connected to. The bottom of container 40 also has a hole 59 to which the liquid reduction level hose 55 is connected to.

As illustrated in FIG. 7, the device has a bottom drain system comprised of an overflow tube 54, whose front end is connected to outlet 60 on the outer face of the container 40 bottom. The container 40 is connected to a level reduction hose 55, whose proximal end is connected to the level reduction hole 59 located at the container bottom 40. The level reduction hose 55 has an occlusion valve 57 therein to allow the drainage of liquid located inside container 40. The ends of overflow hose 54 and level reduction hose 55 may drain into a waste container (not shown), which may be a plastic bag.

Figure 8:
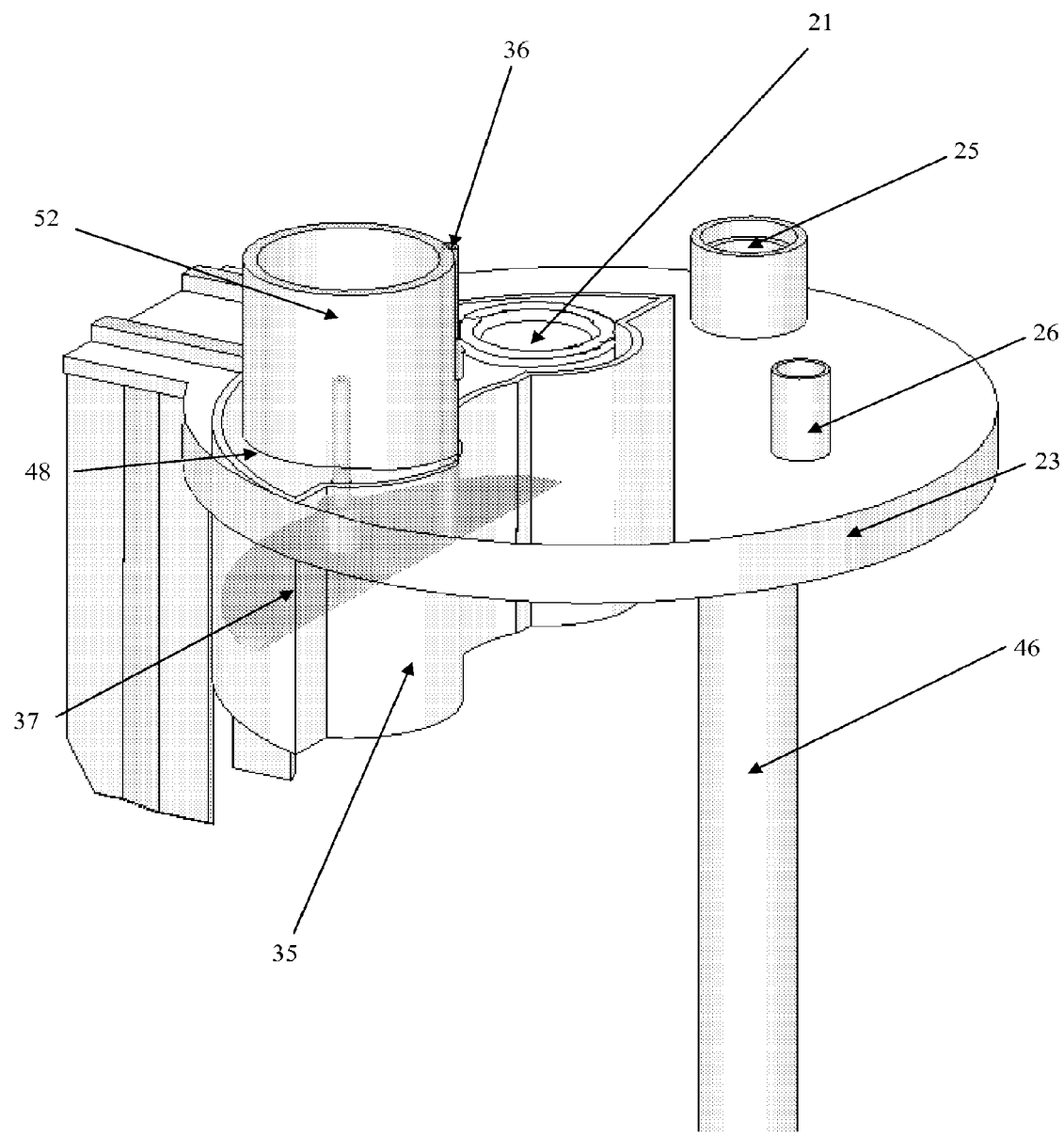
FIG. 8 is an isometric view of the back of the lid attached to the inner heating and humidifying container.

FIG. 8 shows inner container 35 coupled to the bottom of lid 23. The inner container is anchored to supports on lid's 23 bottom face. The inner container 35 can be any size smaller than the container's size 40. Within inner container 35 is a float 37 which is shaped very similar to the inner container 35, but smaller in size, fitting inside thereof. The float has a cylindrical extension 52 which fits into hole 20 of lid 23. Thus, when liquid inside inner container 35 decreases due to evaporation, the float allows for refilling and when the inner container 35 is filled, the float 37 cuts the inflow of liquid. It should be understood that for a person skilled in the art, any other liquid flow control system can be used. Additionally, inner container 35 has a humidifying hose 38.

Figure 9:
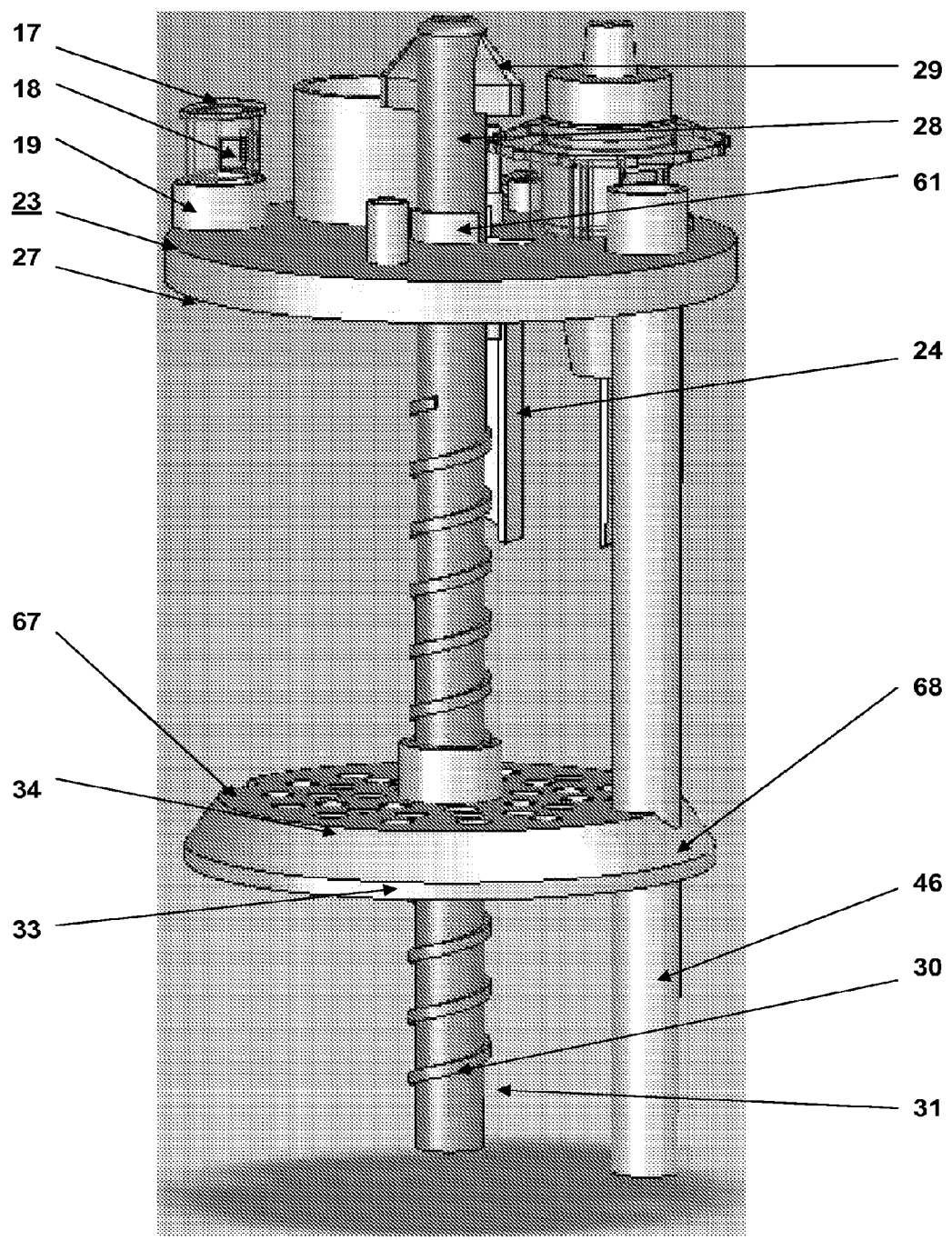
FIG. 9 is a schematic isometric view of the internal elements of the apparatus lid shown in FIG. 5.

FIG. 9 shows the liquid level stabilization mechanism. Said system comprises a level stabilizer 33, which moves axially along the rotating shaft 30. The shift of the level stabilizer 33 is accomplished by turning bulge 29 located at the upper end of the rotating shaft 30. The upper end of shaft 30 passes through lid 23 through hole 61, which additionally permits its stabilization on its longitudinal axis. Similarly, the lower end is inserted into anchor 32 of the container bottom 40 (see FIG. 2).

In the embodiment of the present invention illustrated in FIG. 10, the stabilizer level 33 is formed by one or more perforated surfaces joined together (see FIG. 10b). In the embodiment shown in this figure, two drilling platforms 33a and 33b are used, in which the upper perforated surface 33a has the same diameter or slightly less than the internal diameter of container 40. The outer edge of the upper platform 33a touches the wall of container 40 on which the CPAP level indicator scale 62 is printed or pasted. The perforated upper surface 33a has multiple holes which may be hexagonal or circular; in embodiments different to those shown by this figure, the diameter can vary from 0.1 mm to 7 mm. The bottom face of the upper perforated surface 33a has several insertion slots which allow anchoring of the lower perforated platform 33b between said slots, allowing assembly thereof. The lower perforated platform 33b also has multiple holes 34 may be hexagonal or circular and whose diameter can also vary from 0.1 mm to 7 mm.

When the two drilling platforms 33a and 33b are assembled, both holes do not match. Both the upper perforated platform 33a and lower perforated platform 33b have a hole having an internal thread, which screws to screw 30 of rotating shaft 30. This allows that when rotating shaft 30 rotates, the level stabilizer 33 shifts over the axial length of the rotating shaft 30, essentially by a screw system. The direction of rotation of the shaft 30 will determine the direction of movement of the level stabilizer 33. In this embodiment, the overflow and pressurization tube 44 and bubbling tube 46 stabilize the movement of the perforated platforms of the level stabilizer during its simultaneous movement over rotating shaft 30.

In the embodiment shown in FIG. 10b, the lower perforated platform 33b features multiple grooves on its upper surface, which serve to direct the liquid into the holes of the upper platform 33a.

In another preferred embodiment of the invention, platforms 33a and 33b which make up the level stabilizer, have a hole 67 (shown in FIGS. 9 and 10) for the passage of the overflow and pressurization tube 44 whose internal diameter may be slightly larger than the outside diameter of tube 44, and a hole 68 for the passage of bubbling tube 46, whose internal diameter may be slightly larger than the outside diameter of tube 46. In this embodiment of the invention, the overflow and pressurization tube 44 and bubbling tube 46 stabilize the movement of the perforated platforms of the level stabilizer during its simultaneous movement over rotating shaft 30.

Illustrative Example:

A preferred embodiment of the invention is used, including elements described for FIG. 5. To set a specific pressure, a source of liquid is installed above the level of the device, maintaining the occlusion valve 53 of the level increase hose 52 closed. At this point, the internal container fill hose 52 will let liquid flow towards the inner humidification and heating container 35. This liquid will make the float 37 float on the liquid, which upon reaching the desired level shall occlude hole 20 of lid 23, closing off the passage of liquid. Then, resistance 36 is connected to a conventional power source.

An oxygen source (not shown) is then connected to the conventional connector for hospital gas sources 21 of lid 23. Then, the end of vent tube 6a which is connected to the prongs, is connected to hole 48 of lid 23. The other end of the prongs is connected to another vent tube that connects to hole 25 of lid 23.

Occlusion valve 57 of the level reduction hose 55 must be closed. Then the occlusion valve 53 of the level increase hose 51 is opened, and container 40 is allowed to fill until the liquid level 42 matches the level of CPAP which intends to be provided according to the mark on scale 62. This level can be easily, stably and securely adjusted to an exact or intermediate position.

At that moment, the gas supply is opened to the desired level, producing bubbling in the heating and humidifying container 35 and to a lesser extent, in bubbling hole 47 of bubble tube 46. Then the conventional face mask 7, or nasal prongs 8 are placed in the patient's nostrils.

If the CPAP dose administered needs to be increased, the occlusion valve 53 of the level increase hose 51 must be opened again, and container 40 is filled again until the liquid level 42 matches the CPAP level wished to be administered.

If the CPAP level wishes to be decreased, the occlusion valve 57 of the level reduction hose 55 must be opened until the liquid level 42 matches the CPAP level wishing to be administered.

If the patient needs to be mobilized maintaining the CPAP supply, the front end of resistance 36 is connected to a portable power source. Later, the rotating shaft 30 is driven by rotating it by its top and external end 29, so that the level stabilizer 33 matches the mark on scale 62 to that previously adjusted for the liquid level 42. When the CPAP dose administered is increased or decreased by increasing or decreasing the level of liquid 42 within container 40, the level stabilizer level 33 should be re-positioned by rotating the anchored rotating shaft 30.

Finally, for a better understanding of the cases in which the present invention can be applied, the following official pediatric guides are mentioned as further illustration to the common practices used when attending infants or newborn with respiratory problems. They describe clinical examples with specific values of liquid volume for pressure changes in a patient with a particular clinical situation. Some of these guidelines are:

2005 American Heart Association (AHA) Cardiopulmonary Resuscitation Guidelines for (CPR) and Emergency Cardiovascular Care (ECC) of Pediatric and Neonatal Patients: Neonatal Resuscitation Guidelines. [Pediatrics Official Journal of the American Academy of Pediatrics, Aug. 28, 2006]

Advances in neonatal resuscitation: Supporting transition. [Colin J. Morley and Peter G. Davis, 2008]

A randomized, controlled trial Comparing two Different continuous positive airway pressure systems for the Successful extubation of extremely low birth weight infants. [Pediatrics official journal of the American Academy of Pediatrics, May 23, 2007].

Since many embodiments of the present invention were illustrated in the accompanying drawings, it should be understood that the present invention is not limited to the methods described and illustrated herein, since the present invention comprises many possible variations and modifications which do not depart form the spirit of the invention, which is solely defined by the following claims:

The invention claimed is:

1. A device for controlling pressure level during respiratory treatment, said device regulating the pressure delivered to the patient through a respiratory tool connected to a gas source, wherein said device comprises:
   a container containing a liquid;
   a bubble tube having one end inserted into the liquid in the container and located at a fixed level, and another end connected to the respiratory tool;
   at least one hose for adjusting the liquid level in the container; and
   a stabilization mechanism for stabilizing the liquid level, the stabilization mechanism comprising:
      a container lid;
      a shaft oriented along a longitudinal axis of the container, the shaft having one end connected to the container lid and the other end connected to a bottom of the container; and
      at least one platform configured to move along the longitudinal axis.

2. The device of claim 1, further comprising a second container configured to humidify and heat the gas.

3. The device of claim 2, wherein the second container is found inside the device.

4. The device of claim 1, wherein the device comprises liquid input and output hoses for adjusting the liquid level in the container.

5. The device of claim 1, further comprising a container lid having a hole for allowing the liquid to vent.

6. The device of claim 1, wherein the shaft comprises a screw and the at least one platform comprises an internal hole configured to engage the screw, wherein the at least one platform moves along the longitudinal axis via the screw.

7. The device of claim 1, wherein the platform has holes.

8. The device of claim 7, wherein the holes have a circular shape.

9. The device of claim 1, wherein the stabilizing mechanism comprises two platforms each having holes.

10. The device of claim 7, wherein the platform has an upper surface and one or more grooves on the upper surface, wherein the one or more grooves are configured to direct the liquid towards the holes in the platform.

11. A device for controlling pressure level during respiratory treatment, said device regulating the pressure delivered to the patient through a respiratory tool connected to a gas source, wherein said device comprises:

a container containing a liquid;
a bubble tube having one end inserted into the liquid in the container and another end connected to the respiratory tool;
liquid input and output hoses for changing the liquid level in the container; and
a stabilization mechanism for stabilizing the liquid level, the stabilization mechanism comprising:
  a container lid;
  a shaft oriented along a longitudinal axis of the container, the shaft having one end connected to the container lid and another end connected to a bottom of the container; and
  at least one platform that can move along the longitudinal axis via a screw on the shaft,
wherein the at least one platform has holes.

12. A device for controlling pressure level during respiratory treatment, said device regulating the pressure delivered to the patient through a respiratory tool connected to a gas source, wherein said device comprises:
a container containing a liquid;
a bubble tube having one end inserted into the liquid in the container and another end connected to the respiratory tool;
liquid input and output hoses for changing the liquid level in the container;
a stabilization mechanism for stabilizing the liquid level, the stabilization mechanism comprising:
  a container lid;
  a shaft oriented along a longitudinal axis of the container, the shaft having one end connected to the container lid and another end connected to a bottom of the container;
  at least one platform that can move along the longitudinal axis via a screw on the shaft, wherein the at least one platform has holes; and
a second container configured to humidify and heat the gas, the second container found inside the device.

* * * * *